US00PP12262P2

(12) United States Plant Patent
Sorensen

(10) Patent No.: US PP12,262 P2
(45) Date of Patent: Dec. 11, 2001

(54) OSTEOSPERMUM PLANT NAMED 'AKSULLO'

(75) Inventor: Carl Aksel Kragh Sorensen, Aabyhoj (DK)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/422,167

(22) Filed: Oct. 22, 1999

(51) Int. Cl.[7] ..... A01H 5/00

(52) U.S. Cl. ..... Plt./360
(58) Field of Search ..... Plt./360

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Osteospermum plant named 'Aksullo', characterized by its compact and mounding growth habit; very freely branching; freely flowering habit with numerous inflorescences per plant; large, dark purple, spoon-shaped ray florets and purple disc florets; and good post-production longevity.

1 Drawing Sheet

BACKGROUND OF THE INVENTION

The present invention relates to a new and distinct cultivar of Osteospermum plant, botanically known and *Osteospermum ecklonis*, and hereinafter referred to by the cultivar name Aksullo.

The new cultivar is a product of a planned breeding program conducted by the Inventor in Aabyhoj, Denmark. The objective of the breeding program was to create new Osteospermum cultivars with interesting ray floret colors and spoon-shaped ray florets.

The new cultivar originated from a cross made by the Inventor of a proprietary selection of *Osteospermum ecklonis* identified as code number 9524 as the female, or seed, parent and a proprietary selection of *Osteospermum ecklonis* identified as code number 9518, as the male, or pollen, parent. The new Osteospermum was selected by the Inventor as a flowering plant within the progeny of this cross in a controlled environment in Aabyhoj, Denmark, in 1996.

Plants of the new Osteospermum are more compact and have more ray florets that are darker in color than plants of the female parent, the selection 9524. Compared to ray florets of plants of the male parent, the selection, 9518, ray florets of plants of the new Osteospermum have a more distinct spoon-shape and differ in color.

Asexual propagation of the new cultivar by terminal cuttings at Aabyhoj, has shown that the unique features of this new Osteospermum are stable and reproduced true to type in successive generations.

SUMMARY OF THE INVENTION

The following traits have been repeatedly observed and are determined to be the unique characteristics of 'Aksullo'. These characteristics in combination distinguish 'Aksullo' as a new and distinct cultivar:

1. Compact and mounding growth habit.

2. Very freely branching.

3. Freely flowering with numerous inflorescences per plant.

4. Large, dark purple, spoon-shaped ray florets and purple disc florets.

5. Good post-production longevity.

The new cultivar can be compared to the Osteospermum cultivar Sunny Sonja, disclosed in U.S. Plant Pat. No. 10,341. In side-by-side comparisons conducted in Encinitas, Calif., plants of the new cultivar differ from plants of the cultivar Sunny Sonja in the following characteristics:

1. Plants of the new Osteospermum are larger, more vigorous and have a more spreading plant habit than plants of the cultivar Sunny Sonja.

2. Plants of the new Osteospermum are much more freely flowering than plants of the cultivar Sunny Sonja.

3. Ray and disc florets of plants of the new Osteospermum are darker in color than ray and disc florets of plants of the cultivar Sunny Sonja.

The new cultivar can also be compared to the Osteospermum cultivar Pemba, disclosed in U.S. Plant patent application Ser. No. 09/291,105. In side-by-side comparisons conducted by the Inventor in Aabyhoj, Denmark, plants of the new cultivar differ from plants of the cultivar Pemba in the following characteristics:

1. Plants of the new Osteospermum are more compact than plants of the cultivar Pemba.

2. Ray florets of plants of the new Osteospermum are shorter, broader and darker in color than ray florets of plants of the cultivar Pemba.

The cultivar Aksullo has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colros as true as it is reasonably possible to obtain in colored reproductions of this type.

The photograph at the top of the sheet comprises a side perspective view of a typical flowering plant of 'Aksullo'.

The photograph at the bottom of the sheet is a close-up view of typical inflorescence buds, inflorescences and leaves of 'Aksullo' (left) and 'Sunny Sonja' (right). Foliage and floret colors in the photographs may appear different from the actual colors due to light reflectance.

DETAILED BOTANICAL DESCRIPTION

The following observations, measurements and values describe plants of the new cultivar grown in Encinitas, Calif., during the spring in a polyethylene-covered greenhouse. During the production period, day temperatures ranged from 16 to 21° C., night temperatures ranged from 10 to 16° C., and light levels were about 4,000 foot-candles. Plants were pinched (terminal apex removed) one time. Measurements and numerical values represent averages for typical flowering plants grown in one-gallon containers with two plants per container; plants used for descriptions and the photographs were about 19 weeks old.

Color references are made to The Royal Horticultural Society Colour Chart except where general terms of ordinary dictionary significance are used.

Botanical classification: *Osteospermum ecklonis* cultivar Aksullo.

Parentage:

*Female, or seed, parent.*—Proprietary selection of *Osteospermum ecklonis* identified as 9524.

*Male, or pollen, parent.*—Proprietary selection of *Osteospermum ecklonis* identified as 9518.

Propagation:

*Type.*—By terminal cuttings.

*Time to initiate roots.*—About 10 days at 18° C.

*Time to develop roots.*—About 21 days at 18° C.

*Root description.*—Fibrous.

Plant description:

*Appearance.*—Perennial herbaceous container and garden plant. Compact and mounded plant habit; upright to spreading. Very freely branching, about 17 lateral branches developing after pinching.

*Crop time.*—From planting rooted cuttings, about 14 to 19 weeks are required to produce a finished, flowering plant in a one-gallon container.

*Vigor.*—Moderate.

*Plant height, to top of inflorescence plane.*—About 24 cm.

*Plant spread.*—To outer leaves, about 30 cm; to outer inflorescences, about 35 cm.

*Lateral branch description.*—Length: About 7 cm to 12 cm. Diameter: About 4 mm. Internode length: about 1.2 cm. Texture: Glabrous; woody at base. Color: 146B tinged with 59A.

*Foliage description.*—Leaves alternate, single. Length, fully expanded leaves, basal: About 4.75 cm. Width, fully expanded leaves, basal: About 1.5 cm. Shape: Elliptic. Apex: Broadly acute. Base: Attenuate, sessile. Margin: Entire with occasional irregular teeth. Aspect: Mostly flat. Texture: Tough; upper, smooth; lower, glandular. Fragrance: Faint herb-like scent. Color: Young foliage, upper surface: 147A. Young foliage, lower surface: 147B. Fully expanded foliage, upper surface: 147A. Fully expanded foliage, lower surface: 147B. Attenuated leaf base: 147B. Venation: Upper, 147B; lower surface, 147C.

Inflorescence description:

*Appearance.*—Daisy-type composite inflorescence form; actinomorphic. Single inflorescences displayed just above or beyond foliage, upright to horizontal on long peduncles arising from leaf axils. Disc and ray florets arranged acropetally on a capitulum. Freely flowering, typically about 65 opened and opening inflorescences per plant. Inflorescences last about one week. Inflorescences persistent.

*Flowering response.*—Plants flower continuously from April to October in the Northern Hemisphere.

*Fragrance.*—Not detected.

*Inflorescence size.*—Diameter: About 5.25 cm. Depth (height): About 2 cm. Diameter of disc: About 1.3 cm.

*Inflorescence buds* (*at stage of showing color*).—Length: About 1.8 cm. Width: About 1 cm. Shape: Ovoid. Color: 151A.

*Ray florets.*—Length: About 2.8 cm. Width: Towards base, about 4 mm; midsection, at indentation, about 2 mm; towards apex, 3 mm. Shape: Spoon. Apex: Acute and slightly tri-dentate. Base: Attenuate. Margin: Entire. Aspect: Horizontal. Texture: Smooth, Velvety. Number of ray florets per inflorescence: About 15 in a single whorl. Color: When opening, upper surface: 84A. When opening, lower surface: 83A to 83B. Fully opened, upper surface: 77A floret color does not fade. Fully opened, lower surface: 83A and 93B longitudinal stripes.

*Disc florets.*—Shape: Tubular; five-lobed, fluted at apex. Number of disc florets per inflorescence: Numerous, about 64. Length: About 9 mm. Width: About 2 mm. Color: Immature: 86A to 86B. Mature: 86C.

*Phyllaries.*—Shape: Ligulate, narrow. Length: 1.5 cm. Apex: Sharply acute. Margin: Entire; membranous edges. Quantity and arrangement: About 14 in a single whorl. Color: upper surface. 146B; lower surface, 146A.

*Peduncle.*—Length: Terminal peduncle, about 10 cm; second peduncle, about 8.5 cm. Aspect: Moderately strong; inflorescesnces held above foliage. Primary peduncles, about 45° to vertical. Texture: Somewhat coarse. Color: 146B.

*Reproductive organs.*—Androecium: Present on disc florets only. Stamens: Five. Anther shape: Elongated, oblong. Anther length: About 3 mm. Anther color 83A. Pollen amount: Moderate. Pollen color: 23B. Gynoecium: Present on ray and disc florets. Pistils: One. Pistil length: About 7 mm. Stigma shape: Bipartite. Stigma color: 83A. Style length: About 4 mm. Style color: 83B. Ovary color: 145C.

*Seed.*—Seed development has not been observed.

Disease resistance: Resistance to pathogens common to Osteospermum has not been observed on plants of the new Osteospermum.

It is claimed:

1. A new and distinct cultivar of Osteospermum plant named 'Aksullo', as illustrated and described.

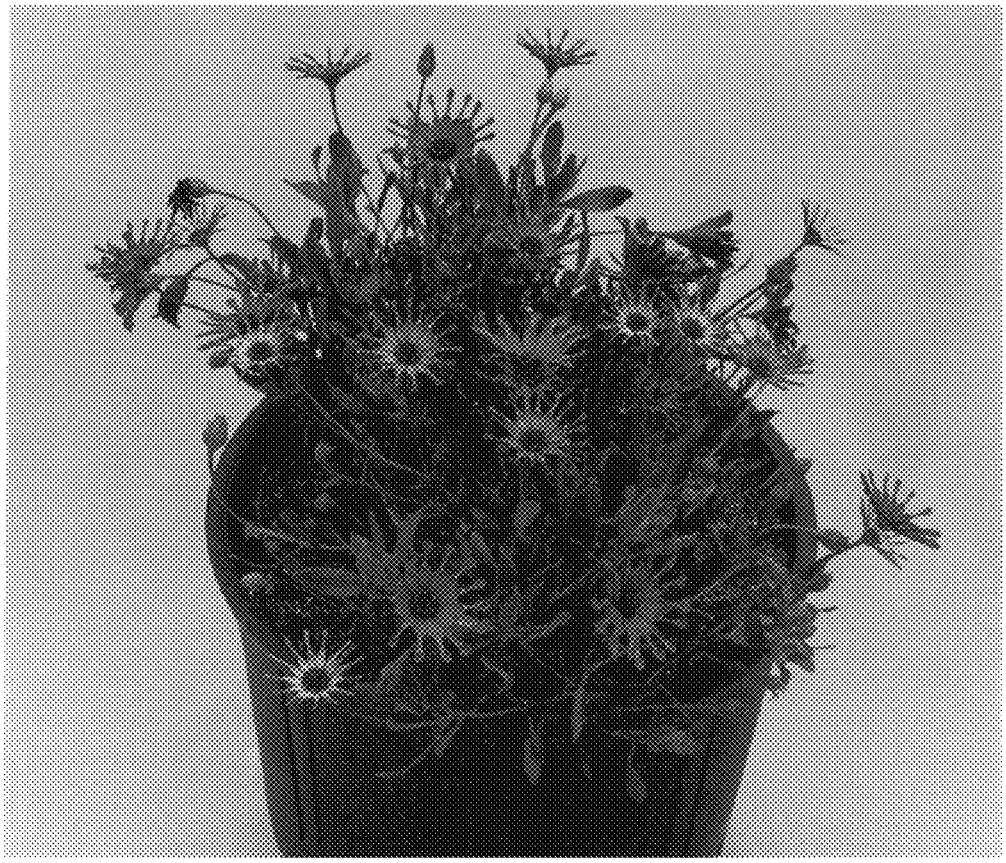
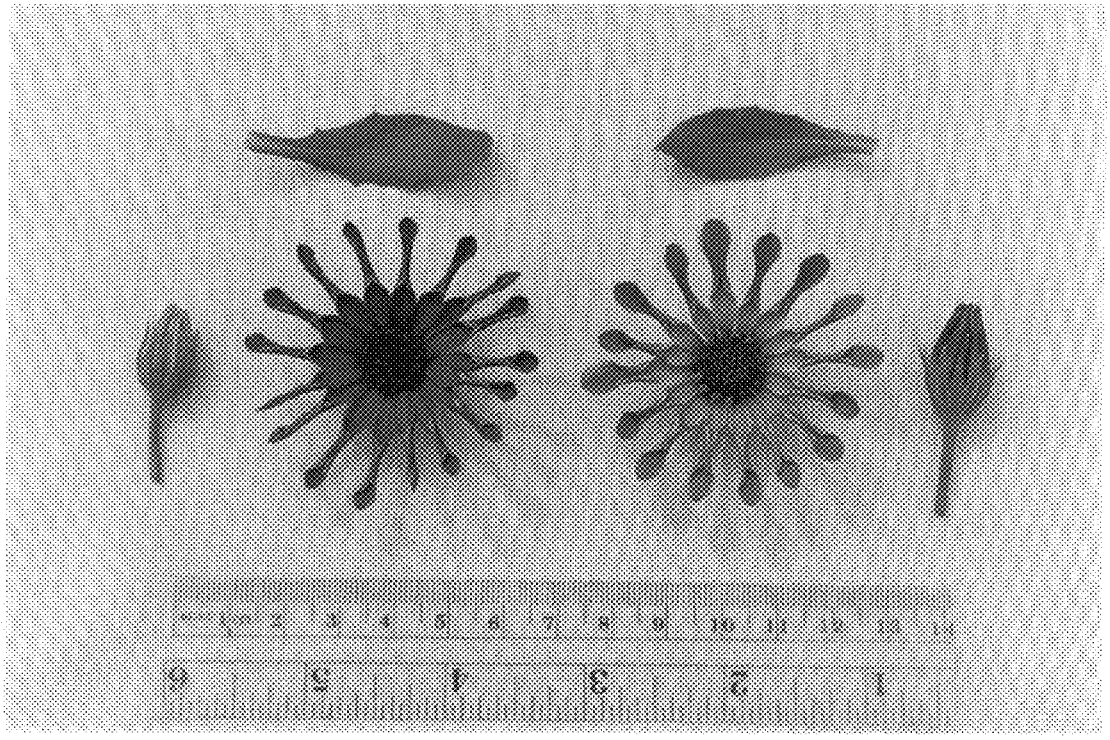

* * * * *